US012064653B2

(12) United States Patent
Jennings

(10) Patent No.: US 12,064,653 B2
(45) Date of Patent: Aug. 20, 2024

(54) WEARABLE CONTINUOUS POSITIVE AIRWAY PRESSURE ASSEMBLY

(71) Applicant: William Jennings, Sandy Springs, GA (US)

(72) Inventor: William Jennings, Sandy Springs, GA (US)

( * ) Notice: Subject to any disclaimer, the term of this patent is extended or adjusted under 35 U.S.C. 154(b) by 625 days.

(21) Appl. No.: 17/370,710

(22) Filed: Jul. 8, 2021

(65) Prior Publication Data

US 2023/0010836 A1 Jan. 12, 2023

(51) Int. Cl.
- A62B 9/04 (2006.01)
- A61F 9/02 (2006.01)
- A62B 7/10 (2006.01)
- A62B 18/00 (2006.01)
- A62B 18/08 (2006.01)
- A62B 7/12 (2006.01)

(52) U.S. Cl.
CPC ............... *A62B 9/04* (2013.01); *A61F 9/029* (2013.01); *A62B 7/10* (2013.01); *A62B 18/003* (2013.01); *A62B 18/006* (2013.01); *A62B 18/084* (2013.01); *A62B 7/12* (2013.01)

(58) Field of Classification Search
CPC . A62B 9/04; A62B 7/00–14; A62B 18/00–10; A61F 9/029; A41D 13/025
See application file for complete search history.

(56) References Cited

U.S. PATENT DOCUMENTS

| 6,772,762 B2 | 8/2004 | Piesinger |
| 7,118,608 B2 | 10/2006 | Lovell |
| 2017/0361133 A1 | 12/2017 | Yu |

FOREIGN PATENT DOCUMENTS

| GB | 2580349 A | * | 7/2020 | ............. A62B 18/02 |
| WO | WO2013082650 | | 6/2013 | |
| WO | WO2015140776 | | 9/2015 | |
| WO | WO-2021220179 A1 | * | 11/2021 | |

* cited by examiner

Primary Examiner — Samchuan C Yao
Assistant Examiner — Kira B Daher

(57) ABSTRACT

A wearable continuous positive airway pressure assembly for protecting a user from breathing airborne particles includes a continuous positive airway pressure machine that has an intake and an exhaust. A pair of shoulder straps is each coupled to the continuous positive airway pressure machine for wearing the continuous positive airway pressure machine on the user's back. An intake hose is fluidly coupled to the intake of the continuous positive airway pressure machine, a filter is fluidly coupled to the intake hose, and an exhaust hose is fluidly coupled to the exhaust of the continuous positive airway pressure machine. A face mask is fluidly coupled to the exhaust hose to receive the pressurized air from the exhaust hose thereby inhibiting the user from breathing ambient air.

5 Claims, 5 Drawing Sheets

WEARABLE CONTINUOUS POSITIVE AIRWAY PRESSURE ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to continuous positive airway pressure device and more particularly pertains to a new continuous positive airway pressure device for protecting a user from breathing airborne particles. The device includes a continuous positive air pressure machine that has shoulder straps for wearing on a user's back. A face shield is included and a face mask is included that is in fluid communication with the continuous positive air pressure machine. The face mask is worn on a user's face to inhibit the user from breathing ambient air and the face shield is worn over the face mask.

(2) Description of Related Art Including Information Disclosed Under 37 CFR 1.97 and 1.98

The prior art relates to continuous positive airway pressure devices including a pair of eyeglasses with air tubes integrated therein that are in fluid communication with a pressurized air source for breathing. The prior art discloses a portable air purifier that includes absorbent elements for absorbing particles from breathing air. The prior art discloses a positive pressure air flow device that includes a respirator and an air filter being integrated into the respirator for filtering breathing air.

BRIEF SUMMARY OF THE INVENTION

An embodiment of the disclosure meets the needs presented above by generally comprising a continuous positive airway pressure machine that has an intake and an exhaust. A pair of shoulder straps is each coupled to the continuous positive airway pressure machine for wearing the continuous positive airway pressure machine on the user's back. An intake hose is fluidly coupled to the intake of the continuous positive airway pressure machine, a filter is fluidly coupled to the intake hose, and an exhaust hose is fluidly coupled to the exhaust of the continuous positive airway pressure machine. A face mask is fluidly coupled to the exhaust hose to receive the pressurized air from the exhaust hose thereby inhibiting the user from breathing ambient air.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
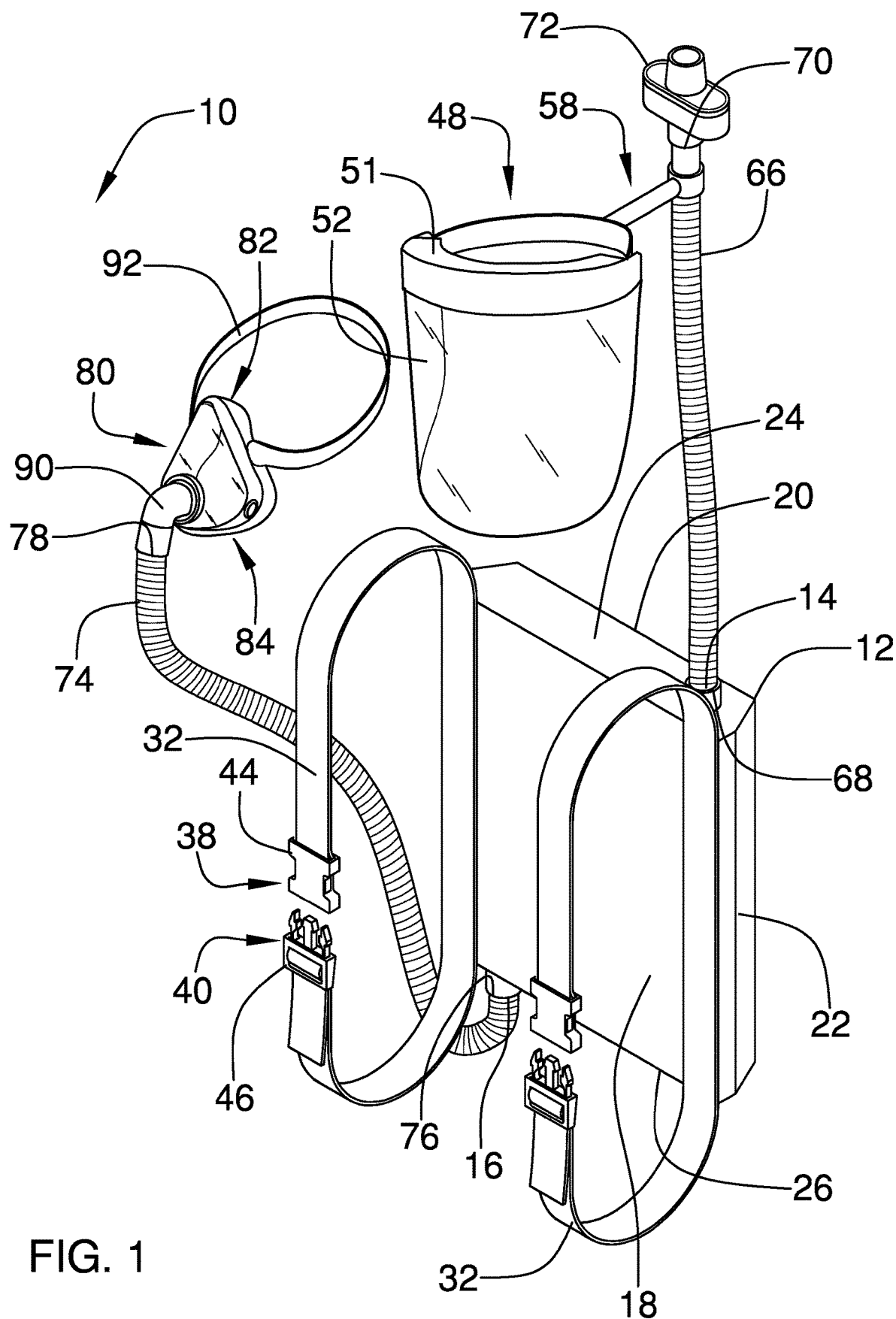
FIG. 1 is a perspective view of a wearable continuous positive airway pressure assembly according to an embodiment of the disclosure.
Figure 2:
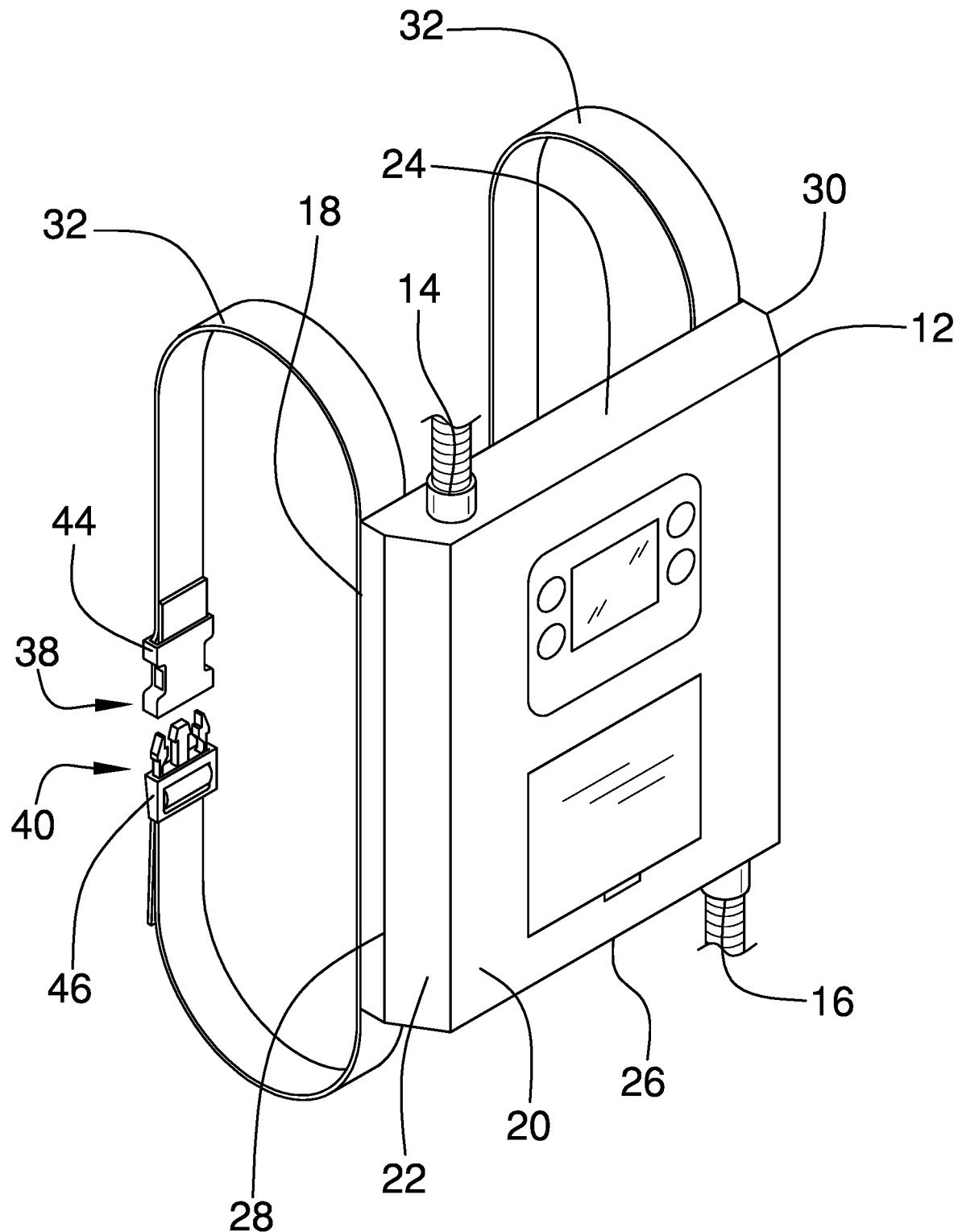
FIG. 2 is a back perspective view of an embodiment of the disclosure.
Figure 3:
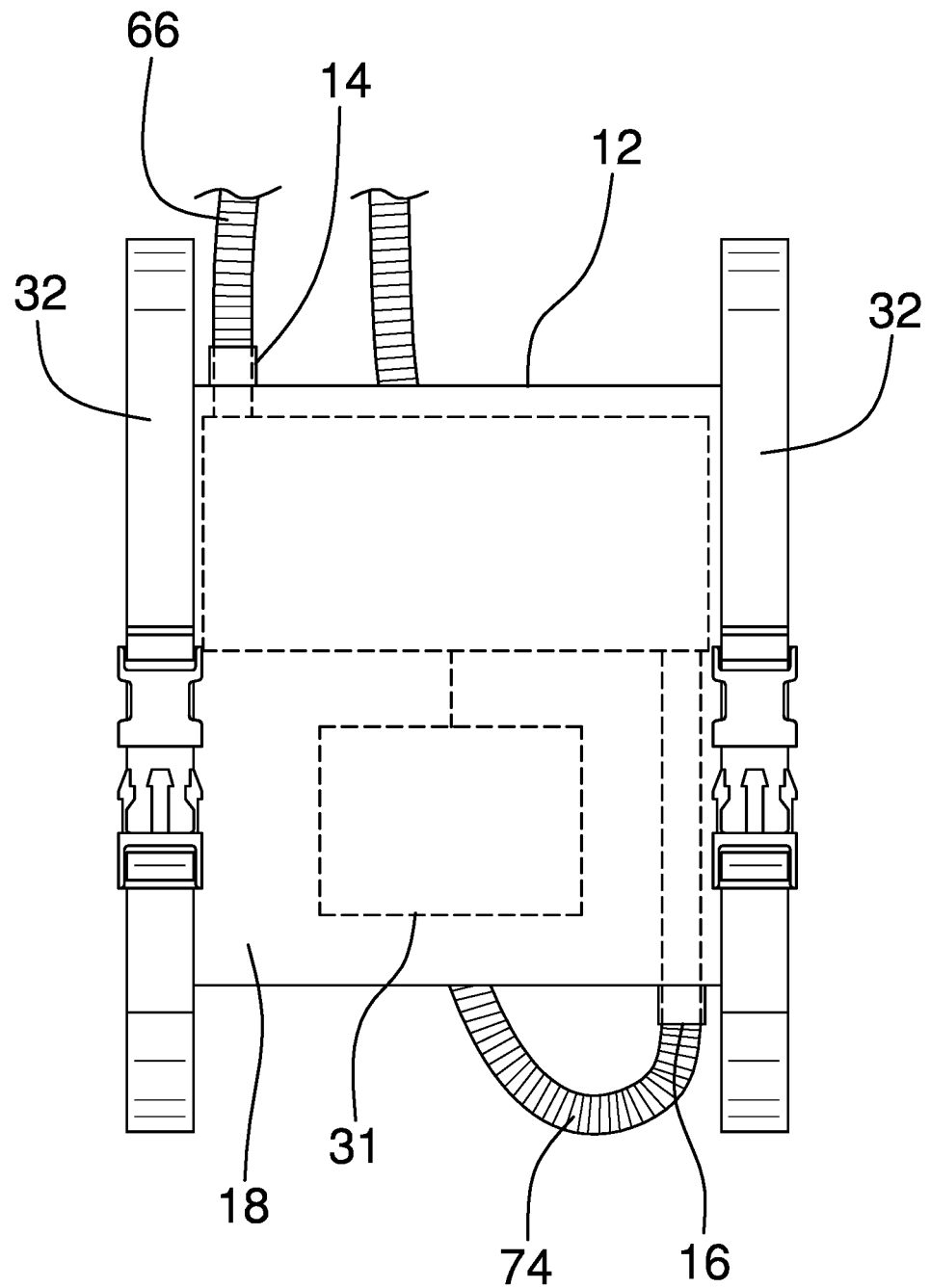
FIG. 3 is a front phantom view of an embodiment of the disclosure.
Figure 4:
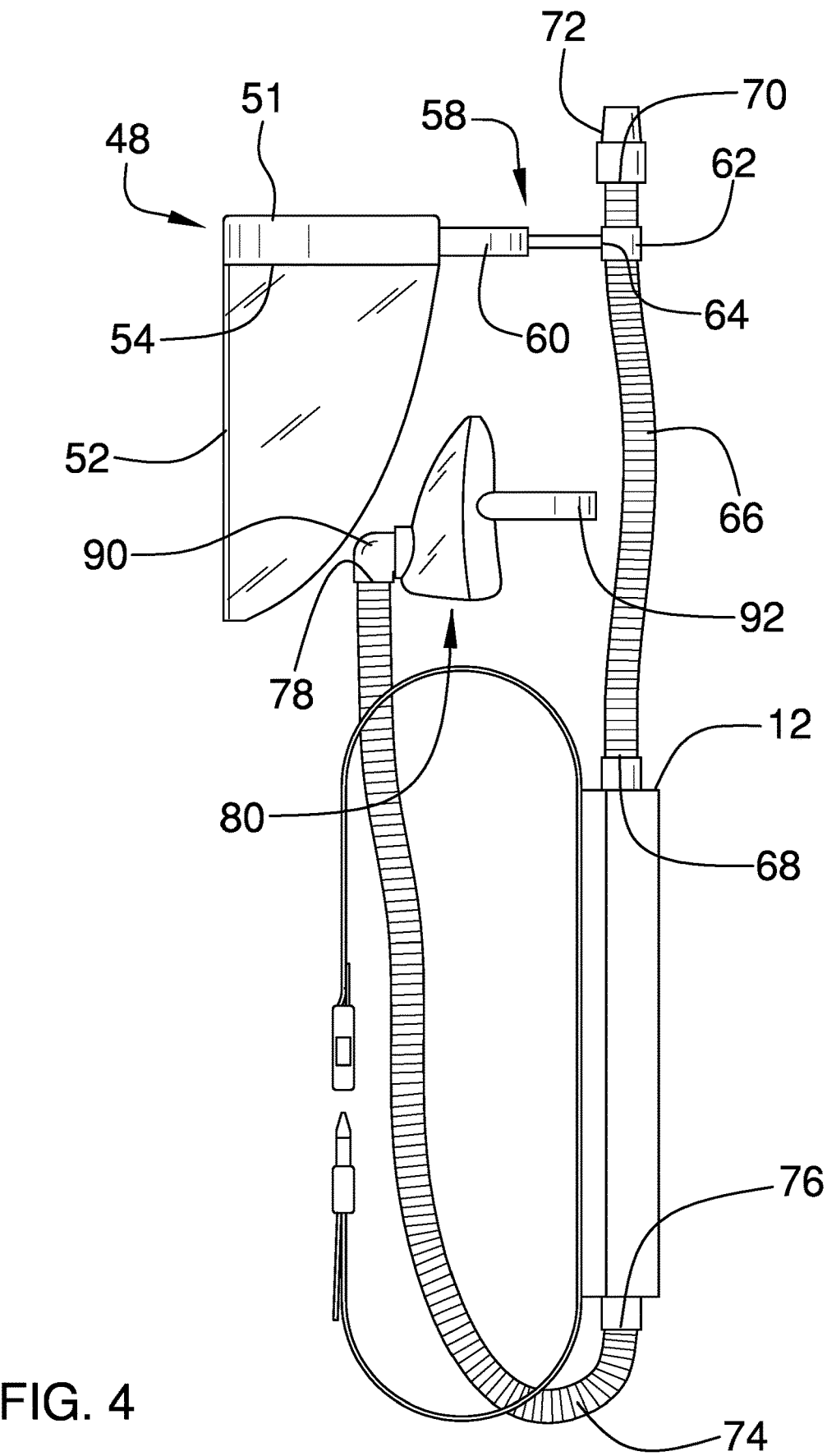
FIG. 4 is a left side view of an embodiment of the disclosure.
Figure 5:
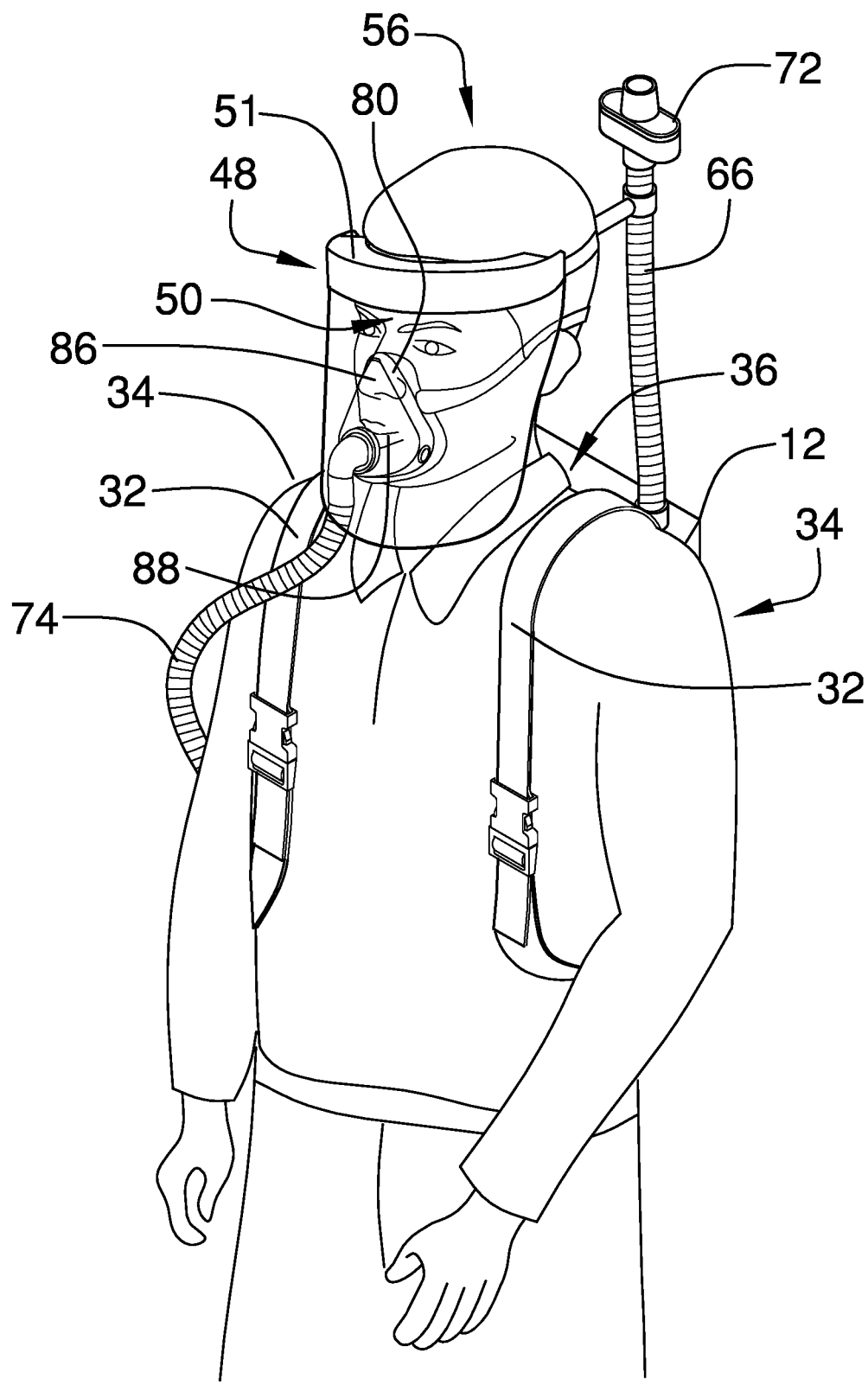
FIG. 5 is a perspective in-use view of an embodiment of the disclosure.

With reference now to the drawings, and in particular to FIGS. 1 through 5 thereof, a new continuous positive airway pressure device embodying the principles and concepts of an embodiment of the disclosure and generally designated by the reference numeral 10 will be described.

As best illustrated in FIGS. 1 through 5, the wearable continuous positive airway pressure assembly 10 generally comprises a continuous positive airway pressure machine 12 that has an intake 14 and an exhaust 16 for urging air inwardly through the intake 14 and outwardly through the exhaust 16. The continuous positive airway pressure machine 12 has front wall 18, a back wall 20 and an outer wall 22 extending between the front wall 18 and the back wall 20, and the outer wall 22 has a top side 24, a bottom side 26, a first lateral side 28 and a second lateral side 30. The intake 14 extends through the top side 24 and the exhaust 16 extends through the bottom side 26. Additionally, as is most clearly shown in FIG. 2, the continuous positive airway pressure machine 12 may be of any conventional design, and may include electronic controls and an electronic display. Additionally, the continuous positive airway pressure machine 12 may include a rechargeable battery 31 for supplying electrical power to the continuous positive airway pressure machine 12.

A pair of shoulder straps 32 is each coupled to the continuous positive airway pressure machine 12. Moreover, each of the shoulder straps 32 can be worn over a user's shoulders 34 for wearing the continuous positive airway pressure machine 12 on the user's back 36. Each of the shoulder straps 32 has a first end 38, a second end 40 and a first surface 42 extending between the first end 38 and the second end 40. The first surface 42 of each of the shoulder straps 32 is coupled to the front wall 18 of the continuous positive airway pressure machine 12. Furthermore, the first end 38 of a respective shoulder strap 32 is matable to the second end 40 of the respective shoulder strap 32 having the respective shoulder strap 32 forming a closed loop. Each of the shoulder straps 32 might include a first mating member 44 coupled to the first end 38 and a second mating member 46 coupled to the second end 40, and the first mating member 44 might releasably engage the second mating member 46. Additionally, each of the first mating member 44 and the second mating member 46 may comprise complementary buckles or the like.

A face shield 48 is provided and the face shield 48 can be worn over the user's face 50. The face shield 48 includes a head band 51 and a window 52 that extends downwardly from a bottom surface 54 of the head band 51. In this way the head band 60 can be worn around the user's head 56 having the window 52 being positioned in front of the user's face 50. A holder 58 is coupled to and extends away from the face shield 48. The holder 58 includes a stem 60 extending rearwardly away from the head band 51 and a sleeve 62 that is positioned on a distal end 64 of the stem 60.

An intake hose 66 is fluidly coupled to the intake 14 of the continuous positive airway pressure machine 12 to direct air into the intake 14. The holder engages the intake hose 66 thereby facilitating the intake hose 66 to be vertically oriented when each of the continuous positive airway pressure machine 12 and the face shield 48 are worn. The intake hose 66 has a first end 68 and a second end 70, and the first end 68 of the intake hose 66 is fluidly coupled to the intake 14. The intake hose 66 extends through the sleeve 62 such that the second end 70 of the intake hose 66 is spaced from the sleeve 62.

A filter 72 is provided and the filter 72 is fluidly coupled to the intake hose 66. In this way the filter 72 can filter particles and microbes from the air passing into the intake hose 66. The filter 72 is positioned on the second end of the intake hose 66 and the filter 72 may comprise a high efficiency particulate air filter or other type of air filter that can filter down to 3.0 microns such that the filter 72 can filter viruses. An exhaust hose 74 is fluidly coupled to the continuous positive airway pressure machine 12 to receive pressurized air from exhaust 16 of the continuous positive airway pressure machine 12. The exhaust hose 74 has a primary end 76 and a secondary end 78, and the primary end 76 is fluidly coupled to the exhaust 16.

A face mask 80 is provided and the face mask 80 is fluidly coupled to the exhaust hose 74 to receive the pressurized air from the exhaust hose 74 thereby. The face mask 80 has a nose portion 82 and a mouth portion 84 to cover the user's nose 86 and the user's mouth 88, respectively, when the face mask 80 is worn. In this way the face mask 80 inhibits the user from breathing ambient air. Thus, the face mask 80 protects the user from airborne bacteria and airborne viruses. The face mask 80 has an inlet 90 and the inlet 90 is fluidly coupled to the secondary end 78 of the exhaust hose 74. A strap 92 is coupled to the face mask 80 such that the strap 92 forms a closed loop for wearing around the user's head 56.

In use, the shoulder straps 32 are worn over the user's shoulders 34 for wearing the continuous positive air pressure machine 12 on the user's back 36. The face mask 80 is worn on the user's face 50 and the face shield 48 is worn on the user's head 56. In this way the air that the user breathes is filtered by the continuous positive air pressure machine 12 and the face shield 48 protects the user's face 50 from airborne particles. Additionally, the positive air pressure in the face mask 80 inhibits the user from breathing ambient air. In this way the user has total protection against inhaling airborne viruses, bacteria or contaminants.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A wearable continuous positive airway pressure assembly for inhibiting a user from inhaling airborne microbes, said assembly comprising:

a continuous positive airway pressure machine having an intake and an exhaust wherein said continuous positive airway pressure machine is configured to urge air inwardly through said intake and outwardly through said exhaust;

a pair of shoulder straps, each of said shoulder straps being coupled to said continuous positive airway pressure machine wherein each of said shoulder straps is configured to be worn over a user's shoulders for wearing said continuous positive airway pressure machine on the user's back;

a face shield being configured to be worn over the user's face;

a holder being coupled to and extending away from said face shield;

an intake hose being fluidly coupled to said intake of said continuous positive airway pressure machine wherein said intake hose is configured to direct air into said intake, said holder engaging said intake hose thereby facilitating said intake hose to be vertically oriented when each of said continuous positive airway pressure machine and said face shield are worn;

a filter being fluidly coupled to said intake hose wherein said filter is configured to filter particles and microbes from the air passing into said intake hose;

an exhaust hose being fluidly coupled to said continuous positive airway pressure machine wherein said exhaust hose is configured to receive pressurized air from said exhaust of said continuous positive airway pressure machine;

a face mask being fluidly coupled to said exhaust hose wherein said face mask is configured to receive the pressurized air from said exhaust hose thereby facilitating the user to breathe the pressurized air; and a strap being coupled to said face mask such that said strap forms a closed loop with said face mask wherein said strap is configured to be worn around the user's head.

2. The assembly according to claim 1, wherein:

said continuous positive airway pressure machine has front wall, a back wall and an outer wall extending between said front wall and said back wall, said outer wall having a top side, a bottom side, a first lateral side and a second lateral side, said intake extending through said top side, said exhaust extending through said bottom side; and each of said shoulder straps has a first end, a second end and a first surface extending between said first end and said second end, said first surface of each of said shoulder straps being coupled to said front wall of said continuous positive airway pressure machine, said first end of a respective shoulder strap being matable to said second end of said respective shoulder strap having said respective shoulder strap forming a closed loop.

3. The assembly according to claim 1, wherein:

said face shield includes a head band and a window extending downwardly from a bottom surface of said head band wherein said head band is configured to be worn around the user's head having said window being positioned in front of the user's face; and said holder includes a stem extending rearwardly away from said head band and a sleeve being positioned on a distal end of said stem.

4. The assembly according to claim 3, wherein:

said intake hose has a first end and a second end, said first end being fluidly coupled to said intake, said intake hose extending through said sleeve such that said second end of said intake hose is spaced from said sleeve;

said exhaust hose has a primary end and a secondary end, said primary end being fluidly coupled to said exhaust; and said face mask has an inlet, said inlet being fluidly coupled to said secondary end of said exhaust hose.

5. A wearable continuous positive airway pressure assembly for inhibiting a user from inhaling airborne microbes, said assembly comprising:

a continuous positive airway pressure machine having an intake and an exhaust wherein said continuous positive airway pressure machine is configured to urge air inwardly through said intake and outwardly through said exhaust, said continuous positive airway pressure machine having front wall, a back wall and an outer wall extending between said front wall and said back wall, said outer wall having a top side, a bottom side, a first lateral side and a second lateral side, said intake extending through said top side, said exhaust extending through said bottom side;

a pair of shoulder straps, each of said shoulder straps being coupled to said continuous positive airway pressure machine wherein each of said shoulder straps is configured to be worn over a user's shoulders for wearing said continuous positive airway pressure machine on the user's back, each of said shoulder straps having a first end, a second end and a first surface extending between said first end and said second end, said first surface of each of said shoulder straps being coupled to said front wall of said continuous positive airway pressure machine, said first end of a respective shoulder strap being matable to said second end of said respective shoulder strap having said respective shoulder strap forming a closed loop;

a face shield being configured to be worn over the user's face, said face shield including a head band and a window extending downwardly from a bottom surface of said head band wherein said head band is configured to be worn around the user's head having said window being positioned in front of the user's face;

a holder being coupled to and extending away from said face shield, said holder including stem extending rearwardly away from said head band and a sleeve being positioned on a distal end of said stem;

an intake hose being fluidly coupled to said intake of said continuous positive airway pressure machine wherein said intake hose is configured to direct air into said intake, said holder engaging said intake hose thereby facilitating said intake hose to be vertically oriented when each of said continuous positive airway pressure machine said face shield are worn, said intake hose having a first end and a second end, said first end of said intake hose being fluidly coupled to said intake, said intake hose extending through said sleeve such that said second end of said intake hose is spaced from said sleeve;

a filter being fluidly coupled to said intake hose wherein said filter is configured to filter particles and microbes from the air passing into said intake hose, said filter being positioned on said second end of said intake hose;

an exhaust hose being fluidly coupled to said continuous positive airway pressure machine wherein said exhaust hose is configured to receive pressurized air from exhaust of said continuous positive airway pressure machine, said exhaust hose having a primary end and a secondary end, said primary end being fluidly coupled to said exhaust;

a face mask being fluidly coupled to said exhaust hose wherein said face mask is configured to receive the pressurized air from said exhaust hose thereby facilitating the user to breathe the pressurized air, said face mask having a nose portion and a mouth portion wherein said face mask is configured to cover the user's mouth and the user's nose when said face mask is worn thereby inhibiting the user from breathing ambient air, said face mask having an inlet, said inlet being fluidly coupled to said secondary end of said exhaust hose; and a strap being coupled to said face mask such that said strap forms a closed loop with said face mask wherein said strap is configured to be worn around the user's head.

* * * * *